United States Patent [19]

Puppe et al.

[11] 4,439,409

[45] Mar. 27, 1984

[54] CRYSTALLINE ALUMINOSILICATE PSH-3 AND ITS PROCESS OF PREPARATION

[75] Inventors: Lothar Puppe, Leverkusen; Jürgen Weisser, Dormagen, both of Fed. Rep. of Germany

[73] Assignee: Bayer Aktiengesellschaft, Leverkusen, Fed. Rep. of Germany

[21] Appl. No.: 368,055

[22] Filed: Apr. 13, 1982

[30] Foreign Application Priority Data

Apr. 30, 1981 [DE] Fed. Rep. of Germany ....... 3117135

[51] Int. Cl.³ .............................................. C01B 33/28
[52] U.S. Cl. .................................. 423/328; 423/329; 260/146 R; 502/60
[58] Field of Search ............................ 423/328, 329; 252/431 N, 455 Z, 260

[56] References Cited

U.S. PATENT DOCUMENTS

| 3,894,107 | 7/1975 | Butter et al. | 260/668 R |
| 3,911,041 | 10/1975 | Kaeding et al. | 260/682 |
| 3,994,105 | 7/1975 | Chang et al. | 260/668 R |
| 4,025,575 | 5/1977 | Chang et al. | 260/682 |
| 4,104,151 | 8/1978 | Rubin et al. | 208/111 |

FOREIGN PATENT DOCUMENTS 2909927 9/1980 Fed. Rep. of Germany .

*Primary Examiner*—Edward J. Meros
*Assistant Examiner*—Jackson Leeds
*Attorney, Agent, or Firm*—Sprung, Horn, Kramer & Woods

[57] ABSTRACT

The present invention relates to a new zeolite material having a composition (molar ratios of the oxides) corresponding to the formula:

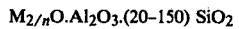

$$M_{2/n}O.Al_2O_3.(20-150) SiO_2$$

(M represents n-valent cation) to a process for the production thereof using hexamethylene imine and to the use of the zeolite material as a catalyst in the conversion of methanol and/or dimethyl ether to hydrocarbons.

2 Claims, No Drawings

CRYSTALLINE ALUMINOSILICATE PSH-3 AND ITS PROCESS OF PREPARATION

This invention relates to a new zeolite-like material, hereinafter termed "PSH-3", to a process for the production thereof and to the use thereof as a catalyst in the production of hydrocarbons from methanol and/or dimethyl ether.

The term "zeolite" refers to water-containing silicate frameworks.

They may be described as a rigid three-dimensional lattice of $SiO_4$- and $AlO_4$-tetrahedra joined by common oxygen atoms. The charge of the $AlO_4$ tetrahedron is negative and is compensated, for example, by an alkali metal or alkaline earth metal cation. The channels in the crystalline aluminosilicates are filled with water molecules which may be removed without the framework collapsing.

It is known to use organic nitrogen compounds for zeolite synthesis. In this case, predominantly $SiO_2$-rich zeolite types are obtained. Zeolites known as "ZSM 5" and "ZSM 11" having particular catalytic properties have become well known recently. A survey of the zeolites obtained using organic cations may be found in "Zeolite Molecular Sieves" by D. W. Breck (Wiley, Interscience (1974), pages 304 to 312 and 348 to 378).

The present invention relates to a new zeolite material, i.e. a crystalline aluminosilicate, having a composition corresponding to the formula (in molar ratios of the oxides):

$$M_{2/n}O.Al_2O_3.(20-150)SiO_2$$

wherein M represents an n-valent cation and having a powder X-ray diagram essentially as indicated in Table 1.

The crystalline aluminosilicate according to the present invention may be obtained from a synthesis mixture containing a silicic acid, an Al compound, alkali and hexamethylene imine.

The zeolite PSH-3 is found from X-ray diffraction data and other characteristics to be different from all formerly known natural and synthetic zeolites.

The zeolite PSH-3 according to the present invention has the following oxidic composition:

$$M_{2/n}OAl_2O_3.(20-150)SiO_2$$

and has a powder X-ray diagram essentially as indicated in Table I.

The $SiO_2/Al_2O_3$ ratio is preferably 30–100. The zeolite PSH-3 has the following composition in the preferably synthesized form:

$$(0.1-0.8)Na_2O(0.2-0.8)R_2O:Al_2O_3:(20-150)SiO_2$$

wherein R represents an organic nitrogen-containing cation derived from hexamethylene imine.

Depending on the production, a mixture of a mineral acid, $Na_2O$, $SiO_2$, $Al_2O_3$, hexamethylene imine and water is formed, which has a composition, in molar ratios of oxides, in the following ranges:

$SiO_2/Al_2O_3 = 10-200$
$OH^-/SiO_2 = 0.05-1.0$
$R/Na_2O = 0.5-5.0$ wherein R represents hexamethylene imine.

Hexamethylene imine is a 7-membered heterocycle containing one nitrogen atom.

The synthesis mixture is preferably obtained in the following ranges:
$SiO_2/Al_2O_3 = 20-150$
$OH^-/SiO_2 = 0.15-0.5$
$R/Na_2O = 1.0-3.0$ The crystalline aluminosilicate zeolite PSH-3 has the following characteristic lines in the X-ray diagram, which are indicated in Table I.

The values were determined by the $K\alpha$-irradiation of the copper. The relative intensities 100 $I/I_o$, wherein $I_o$ represents the intensity of the strongest line, and d, the interplanar space in Å, were determined from the recorded diagram.

The relative intensities are described as follows in Table I.

60–100 very strong
40–60 strong
20–40 medium
0–20 weak

TABLE I

| d-value | Intensity |
|---|---|
| 12.63 | very strong |
| 10.92 | medium |
| 8.84 | very strong |
| 6.86 | weak |
| 6.15 | strong |
| 5.50 | weak |
| 4.91 | weak |
| 4.60 | weak |
| 4.39 | weak |
| 4.09 | weak |
| 3.91 | medium |
| 3.75 | weak |
| 3.56 | weak |
| 3.41 | very strong |
| 3.30 | weak |
| 3.19 | weak |
| 3.11 | weak |
| 2.836 | weak |
| 2.694 | weak |
| 2.592 | weak |
| 2.392 | weak |
| 2.206 | weak |
| 2.122 | weak |
| 2.036 | weak |
| 1.973 | weak |
| 1.873 | weak |
| 1.855 | weak |

The equilibrium adsorption of the crystalline aluminosilicate PSH-3 are listed in the following Table II for a few compounds.

TABLE II

| | Adsorbate in g/100 gadsorbent | |
|---|---|---|
| | $H_2O$ | n-hexane | cyclohexane |
| PSH-3 | 7.7 | 6.9 | 6.1 |

The original cations of the zeolite may be replaced by other cations by means of known ion exchange methods. The exchange preferably takes place after calcination of the zeolite.

The crystalline zeolite is obtained by crystallization of a reaction mixture of the following molar ratios:
$SiO_2/Al_2O_3 = 10-200$
$OH^-/SiO_2 = 0.05-10$
$R/Na_2O = 0.5-5.0$
wherein R represents hexamethylene imine, $(CH_2)_6NH$.

The reaction time is from about 12 to 144 hours, at a temperature of from 80° to 180° C., preferably from 24 to 96 hours at from 110° to 150° C.

The crystalline product obtained is separated from the mother liquor, washed with water to a pH value in running water of from 8 to 10 and dried at 120° C.

If the zeolite PSH-3 is used as an adsorbent or, preferably, as a catalyst, the organic compounds and the water are removed from the channels by conventional methods. This is effected by heating to from 300° to 600° C. in an atmosphere, such as air, nitrogen, ammonia etc., in from 1 to 24 hours.

The starting materials for the production of the zeolite according to the present invention are materials which yield the suitable oxidic compounds. These include, for example, Na-aluminate, Al-sulphate, Al(OH)$_3$, Al$_2$O$_3$, siliceous sol, SiO$_2$-fillers, Na-silicates, NaOH, as well as mineral acids, such as H$_2$SO$_4$ and hexamethylene imine as organic compound.

For further use of the crystalline zeolites as catalysts, a modification is generally necessary, and may be carried out by known methods of ion exchange. The H-form of the zeolite is thus obtained either by the action of dilute acids or by exchange with ammonium salts and subsequent calcination.

Exchanges with transition metal ions, for example from the groups VIIa, VIIIa, Ib and IIb are also possible. Additional exchanges or modifications with main group elements may also be carried out.

For the use according to the present invention, the zeolite PSH-3 is preferably used in the dehydrated H-form. It is also advantageous if a mixture of the H-form with a metal-exchanged form, for example the Mg, Mn, Ba and/or rare earth form, is processed into a catalyst.

The zeolite PSH-3 may be processed into catalysts in a plurality of particle sizes.

Depending on the process adopted (fine dust process, fluidized bed process, travelling bed process, fixed bed process), the particles may be used in the form of a powder, a granulate or as a shaped body.

For the production of the various applications which may be effected by known methods, it is sometimes necessary to process the zeolite PSH-3 described above into technically serviceable catalysts using inert materials and/or binders.

For example, the inert materials and binders, clays, aluminas, bentonites, smectites, naturally occurring or synthetically produced metal oxides, for example aluminum oxide, silicon dioxide, titanium dioxide, zirconium dioxide, thorium oxide, tin oxide, zinc oxide, magnesium oxide and/or beryllium oxide, are suitable for the production of industrial catalysts based on zeolite PSH-3.

The relative proportions of the zeolite components may be varied in wide limits in view of the carrier material used; i.e. in a range of from 1 to 99%, preferably from 10 to 80%, by weight, based on the dry catalyst composition.

The zeolite PSH-3 described above is suitable as a catalyst for the conversion of lower aliphatic alcohols and/or ethers, preferably methanol and/or dimethyl ether to predominantly aliphatically unsaturated hydrocarbons having a low content of aromatic substances.

For example, it is known that methanol and/or dimethyl ether may be transformed over zeolites of the ZSM-5 or ZSM-11 type into water and a hydrocarbon fraction rich in aromatic substances.

For example, U.S. Pat. No. 3,894,107 describes how the hydrocarbon mixture obtained from methanol by zeolite catalysis may consist of 40% and more of aromatic substances. Moreover, U.S. Pat. No. 3,894,105, teaches that the aromatic substances obtained from methanol contain a considerable proportion of 1,2,4,5-tetramethyl benzene (Durol). When using the hydrocarbon mixture obtained from methanol as carburetor fuel, the Durol content in the fraction of aromatic substances is detrimental:

Durol is sparingly soluble in hydrocarbons at room temperature and it tends to crystallize out owing to its high melting point (79.2° C.). It is obvious that this crystallization may cause disturbances during the operation of internal combustion engines which run on fuel produced from methanol. There have been numerous attempts to control the conversion of methanol on zeolites in such a way that the liquid reaction products contain only a little Durol and generally only a few aromatic substances.

For example, the catalyst activity may be reduced by modification of a ZSM-5 zeolite catalyst with organic phosphorus compounds, in such a way that the reaction products are of a predominantly aliphatic nature. However, the production of the catalysts is expensive and industrially unsafe owing to the toxicity of organic phosphines, phosphine oxides, phosphoric acid derivatives etc., (U.S. Pat. No. 3,911,041).

Attempts have also been made to prevent the formation of alkylated aromatic substances by the adjustment of specific processing parameters, for example reduction of the partial pressure of the methanol used. As disclosed, for example, in U.S. Pat. No. 4,025,575, the formation of aromatic substances may be suppressed and the lower olefins increased by dilution of the methanol charge with inert gases. It is obvious that such a procedure is encumbered with technical problems with respect to the space-time yield, return of gas and separation of the reaction products from the inert gaseous substances.

It has now surprisingly been found that the catalytic conversion of methanol and/or dimethyl ether in the presence of the zeolite PSH-3 yields a hydrocarbon mixture having a low content of aromatic substances.

The use according to the present invention of the zeolite PSH-3 as catalyst for the conversion of methanol and/or dimethyl ether may be carried out either batchwise, semi-continuously or continuously. It is immaterial whether the catalyst is fixed or mobile.

The following illustration relates to methanol as charge material. However, it should be noted that dimethyl ether or dimethyl ether-water mixtures may also be used with the same success.

The methanol charge may consist of pure methanol or of water and oxygenate-containing industrial crude methanol. The charge may also be additionally diluted with water.

The process is characterized by the following reaction conditions:

| Range | | Preferred | Particulary preferred |
|---|---|---|---|
| Temperature (°C.) | 200–600 | 250–450 | 300–400 |
| Pressure (bar) | 1–100 | 1–50 | 1–10 |
| Catalyst load (g CH$_3$OH/l.h) | 10–10000 | 100–5000 | 500–2000 |

It may be necessary to free the catalyst used, based on the zeolite PSH-3, from deactivating deposits after a certain operating period. This regeneration is preferably carried out by supplying an oxygen-containing atmosphere (for example air or air-nitrogen mixtures) to the catalyst at an elevated temperature by known methods. The regeneration temperature should not exceed 600° C.

Synthesis gas may similarly be used directly instead of methanol and/or dimethyl ether as charge material to be converted, providing the zeolite PSH-3 is charged with metals which are catalytically suitable for the methanol or Fischer-Tropsch synthesis. Thus the aluminosilicate according to the invention can be used in conjunction with catalysts which are suitable for carbon monoxide hydrogenation. Whereas the fraction of longer-chain hydrocarbons ($C_{5+}$) forming during the customary method of carbon monoxide hydrogenation (Fischer-Tropsch Synthesis with metal-containing catalysts) frequently exhibits up to more than 20-25 C-atoms in the molecule and mainly has a straight-chain structure, the use of the aluminosilicate of the invention as cocatalyst in catalytic carbon monoxide hydrogenation produces, apart from other product constituents a $C_{5+}$ hydrocarbon mixture which for the greater part consists of molecules with 5 to 12 C atoms. When conducting the reaction in an appropriate manner this effect, caused by the aluminosilicate of the invention, of limiting chain length, is associated with the formation of branched hydrocarbons and, possibly, further reactions producing aromatic compounds, whereby, for example, a hydrocarbon mixture produced in such a manner is considerably more suitable for further processing into Otto-carburetor engine fuel than the hydrocarbon mixture produced by the customary method of conducting the Fischer-Tropsch synthesis.

The present invention is described in more detail with reference to the following examples. Percentages relate to percentages, by weight, unless otherwise indicated.

EXAMPLE 1

A mixture of 217 ml of water glass (27% $SiO_2$ and 8% $Na_2O$) and 316 ml of water is mixed with 49.5 g of hexamethylene imine in a 2 liter steel autoclave equipped with a stirrer arrangement and stirred intensively. A solution of 9.22 g of Al-sulphate, 23.4 g of $H_2SO_4$ (concentrated) and 460 ml of water is allowed to flow into this mixture slowly with stirring.

Once the reaction gel formed has homogenized, the mixture is left to crystallize at 150° C. within 70 hours.

At the end of the reaction period, the solid is separated from the liquid phase, washed until the pH is from 7 to 9 and dried at 120° C.

The zeolite has the X-ray diffraction data indicated in the Table and has the following composition after calcination at 500° C.: $0.4Na_2O.Al_2O_3.55SiO_2$.

TABLE

| d (Å) | 100 $I/I_o$ | d (Å) | 100 $I/I_o$ |
|---|---|---|---|
| 12.63 | 100 | 4.39 | 15 |
| 10.92 | 30 | 4.09 | 20 |
| 8.84 | 60 | 3.91 | 30 |
| 6.86 | 5 | 3.75 | 5 |
| 6.15 | 40 | 3.56 | 3 |
| 5.50 | 15 | 3.41 | 100 |
| 4.61 | 1 | 3.30 | 2 |
| 4.60 | 1 | 3.19 | 3 |
| 3.11 | 2 | | |
| 2.836 | 2 | | |
| 2.694 | 3 | | |

TABLE-continued

| d (Å) | 100 $I/I_o$ | d (Å) | 100 $I/I_o$ |
|---|---|---|---|
| 2.592 | 2 | | |
| 2.392 | 2 | | |
| 2.206 | 1 | | |
| 2.122 | 1 | | |
| 2.036 | 2 | | |
| 1.973 | 5 | | |
| 1.873 | 3 | | |
| 1.855 | 5 | | |

EXAMPLE 2

100 g of zeolite PSH-3 in the calcined form are stirred with 1000 ml of 0.5 N HCl for 5 hours at 80° C. The solid material is separated and washed. The exchange is repeated twice more. The H-form of the zeolite may be used as catalyst for the production of hydrocarbons from methanol.

EXAMPLE 3

The mixture as in Example 1 is crystallized at 130° C. over 144 hours. The crystalline product obtained has identical X-ray data to the zeolite PSH-3 from Example 1.

EXAMPLE 4

A mixture of 650 g of silica sol, 790 ml of water and 78 g of NaOH is mixed with 124 g of hexamethylene imine in a 5 liter steel autoclave equipped with a stirrer arrangement. A solution of 23 g of Al-sulphate, 58.5 g of $H_2SO_4$ (concentrated) and 1150 ml of $H_2O$ is charged slowly into this mixture.

The reaction mixture is left to crystallize at 150° C. for 5 days with stirring.

The crystalline solid is separated and washed until the pH is from 8 to 9 in the issuing water. The zeolite has the X-ray diffraction data in Table 1 after calcination.

EXAMPLE 5

Mixture as in Example 1, only the quantity of hexamethylene imine is reduced by 50% in this case. Crystallization takes place over 96 hours at 140° C.

The crystalline end product has predominantly the X-ray data from Table 1, in addition to small amounts of quartz.

EXAMPLE 6

Mixture as in Example 1, only the quantity of Al sulphate is increased to 15 g in this case. The crystalline end product has the following oxidic composition after calcination: $0.2Na_2O, Al_2O_3, 41SiO_2$.

The X-ray data coincide essentially with those in Table 1.

The following Examples 7 and 8 relate to the use of the zeolite PSH-3 prepared in Examples 1 to 6 as a catalyst for the conversion of methanol and/or dimethyl ether to hydrocarbons.

EXAMPLE 7

A zeolite PSH-3 prepared according to Example 1 and decationized according to Example 2 is mixed with 15% of bentonite and processed with water into an extrudable mass. After extrusion, drying at 120° C. and calcination at 500° C., shaped catalyst bodies are obtained. This catalyst material is checked out without applying pressure in an electrically heated tube reactor (d=20 mm, catalyst filling height 160 mm), provided with a preheating zone, as well as inlets for nitrogen and methanol.

The catalyst is brought to a reaction temperature of 370° C. under nitrogen and then charged with methanol vapor in a quantity of 790 g per liter of catalyst per hour.

The methanol conversion is 94.5%, by weight, in this experiment. An organic reaction product having the following composition is obtained in addition to water and unreacted methanol (details in percent, by weight):

| | | |
|---|---|---|
| | methane | 0.9 |
| | ethane | 0.1 |
| | ethene | 2.7 |
| | propane | 2.1 |
| | propene | 11.0 |
| | n-butane | 0.7 |
| | i-butane | 4.2 |
| | n-butene | 7.5 |
| | i-butene | 3.4 |
| | $C_5{}^+$—aliphatic substances (including olefins) | 10.5 |
| | $C_6{}^+$—aromatic substances | 13.0 |
| | dimethyl ether | 13.9 |
| | Total | 100.0 |

As the dimethyl ether formed during the reaction may be recirculated, a carbon selectivity of about 46% is calculated for the total of the $C_5{}^+$-hydrocarbons. When including the $C_4{}^-$-hydrocarbons, this value is increased to about 84%. This shows that zeolite PSH-3 is particularly suitable for the production of an olefin-rich, aliphatic hydrocarbon mixture from methanol.

EXAMPLE 8

This example relates to the conversion of a methanol/dimethyl ether/water equilibrium mixture into predominantly aliphatic olefinic hydrocarbons.

A stream of 50 ml of methanol per hour is conveyed in vapor form without applying a pressure at a temperature of 280° C. over a heap of catalyst consisting of 100 ml of precipitated aluminum oxide granulate. It is known from the literature that aluminum oxide catalyzes the conversion of methanol to dimethyl ether (see, for example, J. B. Senderens, Ann. Chim. Phys. 25, 509 (1912)). The product mixture leaving the reactor is conveyed without further separation over a catalyst based on zeolite PSH-3, prepared in accordance with Examples 1 and 2 and granulated by known methods with an addition of 20% of Montigel.

The contact load is 800 g of charge per liter of catalyst per hour: the conversion temperature is 370° C.

The product stream leaving the reactor has the following composition (without counting the reaction water):

| | | |
|---|---|---|
| | Methane | 1.2 |
| | ethane | 0.1 |
| | ethene | 3.4 |
| | propane | 2.0 |
| | propene | 15.2 |
| | butane | 5.0 |
| | butenes | 7.9 |
| | $C_5{}^+$—hydrocarbons (P + O) | 39.4 |
| | benzene | 0.4 |
| | toluene | 0.4 |
| | $C_8$—aromatic | 1.2 |

-continued

| | |
|---|---|
| substances $C_9{}^+$—aromatic substances | 6.9 |
| dimethyl ether | 16.9 |
| Total | 100.0 |

As the dimethyl ether formed may be recycled, a carbon selectivity of about 47% is calculated for the aliphatic hydrocarbons in the petroleum boiling range ($C_5{}^+$, P+O). This value increases to about 83% providing $C_3$- and $C_4$-hydrocarbons are included. Carburetor fuels may also be obtained from the last-mentioned substances by known methods (alkylation processes).

In the $C_5{}^+$-amount also smaller amounts of oxygen containing components may occur.

EXAMPLE 9

To produce a catalyst for carbon monoxide hydrogenation a suspension of 18.4 g of the aluminosilicate according to the invention in 250 ml of an aqueous solution with 18.4 g potassium waterglass and 70.1 g Fe($NO_3)_3 \times 9H_2O$ is mixed with 160 ml of 11% strength ammonia solution at boiling temperature. The precipitate was filtered off, washed with water until neutral and dried for 4 hours at 150° C. in vacuo (20 mm Hg). After the mixture it was pressed with graphite and bentonite into cylindrical 5×5 mm tablets. Assuming complete precipitation of the iron and quantitative of the potassium waterglass by the precipitate the following catalyst composition is calculated:

| | |
|---|---|
| Fe | 31.5% by weight |
| aluminosilicate according to the invention | 29.6% by weight |
| potassium waterglass | 8.9% by weight |
| bentonite | 20.0% by weight |
| graphite | 10.0% by weight |
| Total | 100.0% by weight |

For the purpose of improving the heat transmission 50 ml of this catalyst for carbon monoxide hydrogenation containing the aluminosilicate according to the invention were mixed with 450 ml of a material (Norton Sc 5232) consisting mainly of solicon carbide and filled into a tube reactor of 25 mm diameter and 150 cm length which has been thermostated with heat-carrying oil. The catalyst filling was first treated for 14 hours at 300° C., under normal pressure and with a gas load of 1000 Nl/(h×l catalyst) and then with carbon monoxide for 8 hours at 300° C. under normal pressure and with a gas load of 1000 Nl (h×l under normal catalyst). The gas loads indicated there and in the following table containing the results of the carbon monoxide hydration refer in all cases to the 50 ml of the above-described catalyst employed. The effect, caused by the aluminosilicate of the invention, of limiting chain length is clear from the data given for the two examples, according to which 95% by weight of the $C_{5+}$ fraction contains $\leq 12$ C atoms in the molecule.

TABLE

| Example | | 9a | 9b |
|---|---|---|---|
| duration of test | h | 12 | 12 |
| temperature of tube wall | °C. | 300 | 310 |
| max. temperature in | °C. | 307 | 324 |

TABLE-continued

| Example | | 9a | 9b |
|---|---|---|---|
| catalyst bed pressure ($H_2 + CO$) | bar | 26,0 | 25,9 |
| $H_2O:CO$ starting ratio | — | 1,05:1 | 1,19:1 |
| gas load ($H_2$ + CO)Nl/(hxl catalyst) | | 1924 | 3039 |
| conversion $H_2$ | % | 62,7 | 58,3 |
| conversion CO | % | 62,2 | 58,8 |
| conversion $H_2$ + CO | % | 62,4 | 58,5 |
| selectivity, based on converted CO | | | |
| $CH_4$ | % | 9,4 | 14,4 |
| $C_{1+}$ | % | 71,5 | 69,3 |
| $CO_2$ | % | 28,5 | 30,7 |
| selectivity based on $C_{1+}$ | | | |
| $CH_4$ | % | 13,6 | 20,7 |
| $C_2H_4$ | % | 0,9 | 1,1 |
| $C_2H_6$ | % | 7,1 | 9,7 |
| $C_3H_6$ | % | 6,9 | 7,5 |
| $C_3H_8$ | % | 4,7 | 5,7 |
| $C_4H_8$ | % | 5,8 | 6,5 |
| $C_4H_{10}$ | % | 2,6 | 3,2 |
| $C_{5+}$ | % | 58,4 | 45,5 |
| distribution of the chain length in $C_{5+}$: | | | |
| proportion up to n-$C_8$—paraffin | % b.wt. | 67 | 67 |
| proportion up to n-$C_{12}$—paraffin | % b.wt. | 95 | 95 |
| proportion up to n-$C_{20}$—paraffin | % b.wt. | 100 | 100 |
| specific yield $C_{1+}$ g/$Nm^3$ converted synthesis gas | | 133 | 119 |
| space/time yield $C_{1+}$ g/(hxl catalyst) | | 256 | 361 |

We claim:

1. A crystalline aluminosilicate having a composition corresponding to the formula (in molar ratios of the oxides):

$$M_{2/n}O \cdot Al_2O_3 \cdot (20-150)SiO_2$$

wherein M represents an n-valent cation and having essentially the following powder X-ray diagram:

| d-value | Intensity |
|---|---|
| 12.63 | very strong |
| 10.92 | medium |
| 8.84 | very strong |
| 6.86 | weak |
| 6.15 | strong |
| 5.50 | weak |
| 4.91 | weak |
| 4.60 | weak |
| 4.39 | weak |
| 4.09 | weak |
| 3.91 | medium |
| 3.75 | weak |
| 3.56 | weak |
| 3.41 | very strong |
| 3.30 | weak |
| 3.19 | weak |
| 3.11 | weak |
| 2.836 | weak |
| 2.694 | weak |
| 2.592 | weak |
| 2.392 | weak |
| 2.206 | weak |
| 2.122 | weak |
| 2.036 | weak |
| 1.973 | weak |
| 1.873 | weak |
| 1.855 | weak |

2. A process for the production of a crystalline aluminosilicate according to claim 1, comprising mixing in water a silicic acid, an aluminum compound, alkali and hexamethylene imine in the range of oxidic molar ratios $SiO_2/Al_2O_3 = 10-200$
$OH^-/SiO_2 = 0.05-1.0$
hexamethylene imine/$Na_2O = 9.5-5.0$, and reacting the reagents for from about 12 to 144 hours at a temperature of from 80° to 180° C., whereupon the aluminosilicate crystallizes out.

* * * * *